United States Patent
Ford

(10) Patent No.: US 7,812,030 B2
(45) Date of Patent: *Oct. 12, 2010

(54) METHODS, COMPOSITIONS, AND KITS FOR ORGAN PROTECTION DURING SYSTEMIC ANTICANCER THERAPY

(75) Inventor: John P. Ford, Unadilla, NY (US)

(73) Assignee: Asymmetric Therapeutics, LLC, Unadilla, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/071,648

(22) Filed: Feb. 25, 2008

(65) Prior Publication Data

US 2008/0207656 A1    Aug. 28, 2008

Related U.S. Application Data

(63) Continuation of application No. 11/196,921, filed on Aug. 3, 2005, now Pat. No. 7,368,456, which is a continuation of application No. 10/918,199, filed on Aug. 13, 2004, now Pat. No. 6,995,165, which is a continuation-in-part of application No. 10/684,203, filed on Oct. 10, 2003, now Pat. No. 6,979,688, which is a continuation-in-part of application No. 10/364,383, filed on Feb. 12, 2003, now abandoned.

(60) Provisional application No. 60/355,764, filed on Feb. 12, 2002.

(51) Int. Cl.
A61K 31/505    (2006.01)

(52) U.S. Cl. .................................................. 514/274
(58) Field of Classification Search ................ None
See application file for complete search history.

(56) References Cited

U.S. PATENT DOCUMENTS

| | | | |
|---|---|---|---|
| 5,326,764 | A | 7/1994 | Milstone et al. |
| 6,979,688 | B2 * | 12/2005 | Ford ............................ 514/274 |
| 6,995,165 | B2 * | 2/2006 | Ford ............................ 514/274 |
| 7,368,456 | B2 * | 5/2008 | Ford ............................ 514/274 |
| 7,662,829 | B2 | 2/2010 | Ford |
| 2003/0158128 | A1 | 8/2003 | Ford |

OTHER PUBLICATIONS (R) Barrows, parts of "Antineoplastic and Immunoactive Drugs," Chapter 86 in Remington: The Science and Practice of Pharmacy, 20th Edition, Gennaro et al. (eds.), Lippincott, Williams & Wilkins, Baltimore, MD, 2000, only pp. 1498 and 1815 supplied.*
Sigma U.S. Catalog, "Biochemical and Reagents for Life Science Research," St. Louis, MO, 2000-2001 edition, only p. 1000 supplied.*
[R] Barrows, parts of "Antineoplastic and Immunoactive Drugs," Chapter 86 in Remington: The Science and Practice of Pharmacy, 20th Edition, Gennaro et al. (eds.), Lippincott, Williams & Wilkins, Baltimore, MD, 2000, only pp. 1498 and 1815 supplied.*

Cao, S. et al., "5-Fluorouracil Prodrug: Role of Anabolic and Catabolic Pathwya Modulaiton in Therapy of Colorectal Cancer", Clinical Cancer Research, vol. 1, pp. 839-845, Aug. 1995.*
Barrows, part of "Antineoplastic and Immunoactive Drugs," Chapter 86 in Remington: The Science and Practice of Pharmacy, 20th Edition, Gennaro et al. (eds.), Lippincott, Williams & Wilkins, Baltimore, Md. 2000, only pp. 1498 and 1815 supplied.
Caco, S. et al., "5-Fluorouracil Prodrug: Role of Anabolic and Catabolic Pathway Modulation in Therapy of Colorectal Cancer," Clinical Cancer Research, Aug. 1995, vol. 1, pp. 839-845.
Childress, J. et al., "Cutaneous Hand and Foot Toxicity Associated with Cancer Chemotherapy," American Journal of Clinical Oncology, Oct. 2003, vol. 26(5), pp. 435-436.
Chua, D. et al., "Efficacy of Capecitabine Monotherapy in Patients with recurrent and Metastic Nasopharyngeal Carcinoma Pretreated with Platinum-Based Chemotherapy," 2003, Proc. Am Soc. Clin. Oncol., vol. 22, p. 511.
Ehrlanger et al., "Cutaneous Absorption and Urinary Excretion of 6-14C-5-5-Fluorouracil Ointment Applicated in an Ointment to Healthy and Diseased Human Skin, "Dermatologica, 1970, vol. 140, Suppl. 1., pp. 129-136.
Elasmer et al. "Case Report: Hand-Foot Syndrome Induced by Oral Fluoropyrimidine S-1", Jpn. J. Clin. Oncol., 2001, vol. 3(4), pp. 172-174.
Findlay, M. et al., "Measurement and Plasma 5-Fluorouracil by High-Performance Liquid Chromatography with Comparison of Results to Tissue Drug Levels Observed Using in Vivo 19F Magnetic Resonance Spectroscopy in Patients in Protracted Venous Infusion With or Without Interferon-α," Annals of Oncology, 1996, vol. 7(47-53), pp. 111-117.
Fischel, J-L. et al., "Experimental Arguments for a Better Understanding of Hand-Foot Syndrome Under Capecitabine," Proceedings of the American Association for Cancer Research, Mar. 2004, vol. 45, p. 487 (Abstract #2119).
Fuji, S. et al., "Effect of Coadministration of Uracil or Cytosine on the Anti-Tumor Activity of Clinical Doses of 1-(2-Tetrahydrofury1)-5-Fluorouracil and Level of 5-Fluorouracil in Rodents," Gann, 70, Apr. 1979, pp. 209-214.
Fukushima, S. et al., "Carcinogenicity of Uracil, a Nongenotoxic Chemical, in Rats and Mice and 1 Rationale," Cancer Research 52, Apr. 1, 1992, pp. 188-193.
Gallo, R. et al., "The Enzymatic Mechanisms for Deoxthymidine Synthesis in Human Leukocites, "The Journal of Clinical Investigation, 1969, vol. 48, pp. 82-93.
Goodman & Gillman, The Pharmacological Basis of Therapeutics, 9th Edition, 1996, pp. 1225-1229.
Hartmann, H.R. et al., "Modulation of the Effects of Fluoropyrimidines on Toxicity and Tumor Inhibition in Rodents by Uridine and Thymidine," Med. Oncol. & Tumor Pharmacother, Apr. 25, 1986, vol. 3(2), pp. 111-118.

(Continued)

Primary Examiner—Lawrence E Crane
(74) Attorney, Agent, or Firm—Dean L. Fanelli; Fanelli Strain & Haag PLLC

(57) ABSTRACT

Methods, compositions, and kits are presented for local tissue protection during systemic administration of anticancer therapeutic agents.

9 Claims, 1 Drawing Sheet

OTHER PUBLICATIONS

Hejna, M. et al., "Decrease of Duration and Symptoms in Chemotherapy-Induced Oral Mucositis by Topical GM-CSF: Results of a Prospective Randomised Trial", European Journal of Cancer, Nov. 2001, vol. 37(16), pp. 1994-2002.

Hirata, K. et al., Pharmacokinetic Study of S-1, a Novel Oral Fluorouracil Antitumor Drug, Clinical Cancer Research, Aug. 1999, pp. 2000-2005, vol. 5.

Hoff, P., "The Tegafur-Based Dihydropyrimidine Dehydrogenase Inhibitory Fluoropyrimidines, UFT/Leucovorin (ORZEL™) and S-1: A Review of Their Clinical Development and Therapeutic Potential," Investigational New Drugs 18, 2000, pp. 163-163.

Ichikawa, W. et al., "Polymorphins of Orotate Phosphoribosyl Transferase (OPRT) Gene and Thymidylate Synthase Tandem Repeat (TSTR) Predic Advese Events (AE) in Colorectal Cancer (CRC) Patients Treated with 5-Fluorouracil (FU) Pluis Leucovorin (LV)," Gastrointestinal Cancer, 2003, p. 1063.

Ichikawa, W. et al., "Both Gene Expression for Orotate Phosphoribosyltransferase and Its Ratio to Dihydropyrimidine Dehydrogenase Influence Outcome Following Fluoropyrimidine-Based Chemotherapy for Metastatic Colorectal Cancer," British Journal of Cancer, (2003), 89 2003 Cancer Research UK.

Ikenaka, K. et al., "Effect of Uracil on Metabolism of 5-fluorouracil in Vitro," Gann, 70, Jun. 1979, pp. 353-359.

Johnson, M. et al., "Life-Threatening Toxicity in a Dihydropyrimidine Dehydrogenase-Deficient Patient after Treatment with Topical 5-Fluorouracil," Clinical Cancer Research, Aug. 1999, vol. 5, pp. 141-146.

Kawaguchi, Y. et al., "Studies on the Metabolism of 1-(2-Tetrahydrofuryl)-5-Fluorouracil and Uracil Co-Administered Orally to Tumor-Bearing Rats," Gann, 71, Dec. 1980, pp. 889-899.

Leo, S. et al., "Dermatological Toxicity from Chemotherapy Containing 5-Fluorouracil," Journal of Chemotherapy, 1994, vol. 6(6), pp. 2-5.

Levy, S. et al., "A Pharamcokinetic Evaluation of 0.5% and a 5% Fluorouracil Topical Cream in Patients with Actinic Keratosis," Clinical Therapeutics, 2001, vol. 23(6), pp. 908-920.

Luccioni, et al., "Pyrimidine Nucleotide Metabolism in Human Colon Carcinomas: Comparison of Normal Tissues Primary Tumors and Xenografts," Int. J. Cancer: 58, 1994, pp. 32-37.

Makean, M. et al., "Phase I and Pharmacologic Study of Intermittent Twice-Daily Oral Therapy with Capecitabine in Patients with Advanced and/or Metastatic Cancer," Journal of Clinical Oncology, 1998, vol. 16(9), pp. 2977-2985.

Maehara, Y. et al., "Scientific Basis for the Combination of Tegafur with Uracil," Oncology, vol. 11(9), Supplement No. 10 pp. 14-21, Sep. 1997.

Malet-Martino, M. et al., "Clinical Studies of Three Oral Prodrugs fo 5-Fluorouracil (Capecitabine, UFT, S-1): A review," The Oncologist, 2002, pp. 288-323.

Niedzwicki, J. et al., "Structure-Activity Relationship fo Pyrimidine Base Analogs as Ligands of Orotate Phosphoribosyltransferase," Biochmical Pharmacology, 1984, vol. 33(15), pp. 2383-2395.

Naguib et al., "Enzymes of Uracil Catbolism in Normal and Neoplastic Human Tissues," Cancer Research 45, Nov. 1985, pp. 5405-5412.

Powis, G., "Anticancer Drugs: Antimetabolite Metabolism and Natural Anticancer Agents," International Encyclopedia of Pharmacology and Therapeutics, 1994, pp. 42-50.

Samid, D., "Important Information About Xeloda (Capecitabine) Tablets," Roche Laboratories Inc., Aug. 2003.

Sawada, N. et al., "Induction of Thymidine Phosphorylase Activity and Enhancement of Capecitabine Efficacy by Taxol/Taxotere in Human Cancer Xenografts," Clinical Cancer Research, Apr. 1998, vo. 4., pp. 1013-1019.

Schilsky, R. L. et al., "Sixty-Third Meeting of the Oncologic Drug Advisory Committee," Food and Drug Administration Center for Drug Evaluation and Research, Sep. 16, 1999.

Senff, H. et al., "Topical 5-Fluorouracil Solution in the Treatment of Warts—Clinical Experience and Percutaneous Absorption," British Journal of Dermatology 118, 1988, pp. 409-414.

Sludden, J. et al., "Liver Dihydropyrimidine Dehydrogenase Activity in Human, Cynomolgus Monkey, Rhesus Monkey, Rhesus Monkey, Dog, Rat and Mouse," Pharmacology, 1998, pp. 276-280.

Stein, J. H.., Editor-in-Chief, Internal Medicine, $4^{th}$ Edition, Chapters 71 and 72, 1994.

Wang, J. et al., "Oral 5-FU is a More Effectivee Antimetastatic Agent that UFT," Anticancer Research 24, 2004, pp. 1353-1360.

Unknown, "Lower Dose Capecitabine is Active and Has Favorable Safety Profile in Elderly Patients with Advanced Breast Cancer," Oncology News International, Aug. 2003, p. 40.

Unknown, "Xeloda (Capecitabine) Tablets Product Label Insert," Roche Pharmaceuticals, Apr. 2003.

Spicer et al., "Toxicity Study of Uracil in Dogs", Journal of Applied Toxicology, vol. 5 (1985), pp. 199-204.

John P. Ford, U.S. PTO Office Action, U.S. Appl. No. 12/073,424, Dec. 12, 2008, 12 pgs.

John P. Ford, U.S. PTO Notice of Allowance, U.S. Appl. No. 12/073,424, Oct. 13, 2009, 10 pgs.

John P. Ford, U.S. PTO Notice of Allowance, U.S. Appl. No. 11/196,921, Dec. 12, 2007, 16 pgs.

John P. Ford, U.S. PTO Office Action, U.S. Appl. No. 11/196,921, Aug. 17, 2007, 10 pgs.

John P. Ford, U.S. PTO Office Action, U.S. Appl. No. 11/196,921, Nov. 29, 2006, 13 pgs.

Hirata Koichi et al., "Pharmacokinetic Study of S-1, a Novel Oral Fluorouracil Antitumor Drug", Clinical Cancer Research, vol. 5 (1999), pp. 2000-2005.

W. Ichikawa et al., "Polymorphins of Orotate Phosphoribosyl Transferase (OPRT) Gene and Thymidylate Synthase Tandem Repeat (TSTR) Predict Adverse Events (AE) in Colorectal Cancer (CRC) Patients Treated with 5-Fluorouracil (FU) Pluis Leucovorin (LV)", Gastrointestinal Cancer (2003), p. 1063.

W. Ichikawa et al., "Both Gene Expression for Orotate Phosphoribosyltransferase and its Ratio to Dihydropyrimidine Dehydrogenase Influence Outcome Following Fluoropyrimidine-Based Chemotherapy for Metstatic Colorectal Cancer", British Journal of Cancer, vol. 89 (2003), Cancer Research UK.

J. Niedzwicki et al., "Structure-Activity Relationship of Ligands of the Pyrimidine Nucleoside Phosphorylases", Biochemical Pharmacology, vol. 32, No. 3 (1983), pp. 399-415.

D. Samid, "Important Information About Xeloda (Capecitabine) Tablets", Roche Laboratories Inc., Aug. 2003.

R.L. Schilsky et al., "Sixty-Third Meeting of the Oncologic Drug Advisory Committee", Food and Drug Administration Center for Drug Evaluation and Research, Sep. 16, 1999.

J.H. Stein, Editor-in-Chief, Internal Medicine, $4^{th}$ Edition, Chapters 71 and 72 (1994), pp. 699-715.

Unknown, "Xeloda (Capecitabine) Tablets Product Label Insert", Roche Pharmaceuticals, Apr. 2003.

John P. Ford, U.S. PTO Office Action, U.S. Appl. No. 10/918,199, Feb. 2, 2005, 20 pgs.

John P. Ford, U.S. PTO Notice of Allowance, U.S. Appl. No. 10/918,199, Sep. 16, 2005, 13 pgs.

J.M. Hageboutrous et al., "Life threatening toxicity in a dihyropyrimidine dehydrogenase-deficient patient after treatment with topical 5-fluorouracil", Clinical Cancer Research, vol. 5 (1999), pp. 2006-2011.

D. Hatfield et al., "Synthesis of (3-Ribosyluric Acid) 5'-Phosphate and (3-Ribosylxanthine) 5'-Phosphate by a Pyrimidine Ribonucleotide Pyrophosphorylase of Beef Erythrocytes", The Journal of Biological Chemistry, Aug. 1964, pp. 60-66.

John P. Ford, U.S. PTO Office Action, U.S. Appl No. 10/684,203, Jun. 7, 2004, 9 pgs.

John P. Ford, U.S. PTO Office Action, U.S. Appl. No. 10/684,203, Dec. 8, 2004, 18 pgs.

John P. Ford, U.S. PTO Notice of Allowance, U.S. Appl. No. 10/684,203, Mar. 17, 2005, 9 pgs.

John P. Ford, U.S. PTO Office Action, U.S. Appl. No. 10/364,383, Aug. 28, 2003, 7 pgs.

John P. Ford, U.S. PTO Office Action, U.S. Appl. No. 10/364,383, Jun. 7, 2004, 7 pgs.

John P. Ford, U.S. PTO Office Action, U.S. Appl. No. 11/146,883, Apr. 29, 2010, 7 pgs.

John P. Ford, U.S. PTO Office Action, U.S. Appl. No. 11/146,883, Aug. 17, 2009, 6 pgs.

John P. Ford, U.S. PTO Office Action, U.S. Appl. No. 11/146,883, Jul. 9, 2008, 6 pgs.

John P. Ford, U.S. PTO Office Action, U.S. Appl. No. 11/146,883, Oct. 25, 2007, 5 pgs.

John P. Ford, U.S. PTO Office Action, U.S. Appl. No. 11/146,883, Nov. 29, 2006, 5 pgs.

John P. Ford, U.S. PTO Office Action, U.S. Appl. No. 12/114,602, Aug. 11, 2009, 8 pgs.

John P. Ford, U.S. PTO Office Action, U.S. Appl. No. 12/114,602, Oct. 31, 2008, 6 pgs.

* cited by examiner

METHODS, COMPOSITIONS, AND KITS FOR ORGAN PROTECTION DURING SYSTEMIC ANTICANCER THERAPY

CROSS-REFERENCE TO RELATED APPLICATIONS

This application is a continuation of U.S. application Ser. No. 11/196,921, which was filed Aug. 3, 2005, and issued as U.S. Pat. No. 7,368,456, which is a continuation of U.S. application Ser. No. 10/918,199, filed Aug. 13, 2004, and issued as U.S. Pat. No. 6,995,165, which is a continuation-in-part of U.S. application Ser. No. 10/684,203, filed Oct. 10, 2003, and issued as 6,979,688, which is a continuation-in-part of U.S. application Ser. No. 10/364,383, filed Feb. 12, 2003, which was abandoned, and claims priority to U.S. Provisional Application No. 60/355,764, filed on Feb. 12, 2002.

BACKGROUND OF THE INVENTION

Systemic administration of antineoplastic chemical agents has been a mainstay of cancer treatment for the past 50 years. But despite success against an ever greater number of cancers, systemic administration of these toxic agents is often attended by deleterious side effects that limit their clinical usefulness.

For example, the antimetabolite fluorinated pyrimidines, among the earliest-introduced of the chemotherapeutic agents, remain front-line treatment for a variety of cancers 40 years after their clinical introduction.

The prototype is 5-fluorouracil (5-FU), which is typically administered parenterally, either by bolus or continuous infusion.

Oral administration of 5-FU is disfavored due to the high activity in the gut wall of dihydropyrimidine dehydrogenase (DPD), the rate-limiting enzyme in 5-FU catabolism. To bypass this problem, orally administrable fluoropyrimidine derivatives have been developed, either in the form of 5-FU precursors, or "prodrugs" (e.g., tegafur, Carmofur, capecitabine, and doxifluridine), or as coadministered combinations of prodrugs with DPD competitors or inhibitors (e.g. UFT, S-1, or Emitefur). Tegafur (FTORAFUR®) (1-(2-tetrahydrofuryl)-5-fluorouracil), is a congener of fluorouracil that introduces a tetrahydrofuran residue in place of the deoxyribose residue in the 5'-deoxy-5-fluorouridine (5'-FUDR) molecule. Carmofur, another orally administrable fluoropyrimidine prodrug, is 1-hexylcarbamoyl-5-fluorouracil (also known as HCFU). Capecitabine (XELODA®, Roche Pharmaceuticals) is a rationally designed fluoropyrimidine carbamate prodrug of 5'-FUDR that can be given orally.

Metabolism of 5-FU and of its prodrugs is complex.

With reference to FIG. 1, tegafur, administered orally, is converted in the liver to 5-fluorouracil ("FU") by action of cytochrome P450.

Capecitabine is converted to 5-FU in a multistep process. In the liver, a 60 kDa carboxyesterase hydrolyzes much of the compound to 5'-deoxy-5-fluorocytidine (5'-DFCR). Cytidine deaminase, an enzyme found in most tissues, including tumors, subsequently converts 5'-DFCR to 5'-deoxy-5-fluorouridine (5'-DFUR). The enzyme thymidine phosphorylase (TP) then hydrolyzes 5'-DFUR to the active drug 5-FU.

Within the cell, 5-FU can be converted to cytostatic (and/or cytotoxic) metabolites by any one or more of three main "anabolic" pathways, each catalyzed by a different enzyme. As labeled in FIG. 1, pathway 1 involves the action of orotate phosphoribosyl transferase (OPRT), pathway 2 activates 5-FU via uridine phosphorylase (UP), and pathway 3 requires the enzyme thymidine phosphorylase (TP). These three pathways interconnect, converging on two principal mechanisms of cell toxicity.

In the first, circled and labeled "a" at the right of FIG. 1, 5-FU is ultimately metabolized to 5-FUTP, which is incorporated during transcription into RNA. Currently, it is thought that the toxicity results from the accumulation of fluorouracil residues in a wide variety of mRNAs coding for many different proteins, rather than from alteration of any single cellular function.

The second principal mechanism of cell toxicity results from anabolic activation of 5-FU to 5-FdUMP. As circled and labeled "b" in FIG. 1, 5-FdUMP forms a ternary complex with thymidine synthase (TS) and the cofactor 5,10-methylene tetrahydrofolate ($CH_2THF$). Tight complexation sequesters TS, preventing the TS-mediated enzymatic formation of dTMP; this, in turn, decreases the synthesis, and thus availability, of thymidine triphosphate (dTTP), which is required for DNA replication and repair. Depletion of dTTP acts as a cytostatic brake on cell growth and division; more recently, it has been suggested that depletion of dTTP may directly trigger programmed cell death (apoptotic) pathways.

Catabolic inactivation of 5-FU is conceptually simpler than anabolic activation, with greater than 80% of an injected dose of 5-FU rapidly degraded by a single pathway, the first and rate-limiting step of which is catalyzed by dihydropyrimidine dehydrogenase (DPD) (also known, synonymously, as uracil reductase, dihydrouracil dehydrogenase, and as dihydrothymine dehydrogenase). The principal byproduct of catabolism, F-β-alanine, is circled and labeled "c" in FIG. 1.

Given the complex interrelatedness of the metabolic pathways, the clinical efficacy of 5-FU and its orally-administrable prodrugs depends, to a first, crude, approximation on the relative activities of the DPD-mediated catabolic pathway and each of the three principal anabolic pathways. But despite intensive study, the extent to which any of these pathways predominates in human tumors is unknown and is likely to vary across tumor types and with different modes and doses of drug administration. Malet-Martino et al., *The Oncologist* 7:288-323 (2002); Ichikawa et al., *Brit. J. Cancer* 89:1486-1492 (2003)

The situation becomes more complex when considering the concurrent and interacting effects of multiple, competing, substrates on the multiple and competing catabolic and anabolic enzymes in the fluoropyrimidine pathway. Further complexity is added by variation in the activity of these enzymes among a genetically diverse human population, with plasma levels of 5-FU varying by about three orders of magnitude among humans exposed to the same dose of 5-FU.

UFT is a combination of uracil and ftorafur in a 4:1 molar ratio. UFT is approved for clinical use in Europe and Japan; it has been denied FDA approval for clinical marketing in the U.S.

After oral ingestion, the ftorafur component of UFT is metabolized by P450 to 5-FU. The uracil component is intended to compete with 5-FU for degradation by DPD; present at a several-fold molar excess over ftorafur in the administered composition, and thus intended to be present at a several-fold molar excess over ftorafur (and thus 5-FU) in tissues, uracil is intended to outcompete 5-FU for reaction with DPD, inhibiting DPD catabolic inactivation of 5-FU. The intended result is a higher circulating level of 5-FU, leading to greater 5-FU-mediated cytotoxicity. Cao et al., *Clinical Cancer Res.* 1:839-845 (1995).

But the actual in vivo concentrations of uracil and 5-FU after UFT administration do not invariably follow the intended ratio. Administration of UFT to rats results in a greater than 1000-fold variation in uracil level within various organs, and can lead to up to a 100-fold excess of uracil over 5-FU in some tissues. (Kawaguchi et al., *Gann.* 71(6):889-99. (1980)).

Furthermore, uracil can also compete with 5-FU for reaction with the three principal anabolic activating enzymes. In order for the UFT combination to show greater clinical efficacy than ftorafur alone, uracil must not outcompete 5-FU for activation by at least one of OPRT, TP, and UP in the tumor. The outcome thus depends upon the relative amount of each of the four principal rate-limiting enzymes in each of the cells and tissues taking up 5-FU, and on the relative affinity of each of the enzymes for uracil and 5-FU. The latter depends, in turn, at least in part on cellular pH: OPRT, for example, favors 5-FU over uracil by about 50 times at neutral pH.

Variation in the relative amounts of each of the four principal rate-limiting enzymes among tissues and tumors makes a priori prediction of UFT efficacy in any particular tumor unreliable. And experiments in laboratory animals provide little help: the relative affinities of these enzymes for 5-FU and for uracil differ substantially among different animal species, and particularly among different animal tumors.

Sludden et al. report, for example, that liver DPD activity is highly variable within and among tested species. Sludden et al., *Pharmacology* 56:276-280 (1998). At least one study reports that 5-fluorouracil is a better substrate for human dihydrouracil dehydrogenase (DPD) than is uracil, Naguib et al., *Cancer Research* 45:5405-5412 (1985).

And as complex as the physiology of fluoropyrimidine metabolism may be with respect to desired antitumor effects, the pathophysiology of fluoropyrimidine side-effects is even less well understood.

Among these poorly understood side effects of fluoropyrimidine administration, the physiology of hand-foot syndrome ("HFS", "palmar-plantar erythrodysesthesia", "PPES") is perhaps the most obscure.

HFS usually starts with numbness, tingling, redness, and painless swelling of the hands and/or feet. Grade 1 HFS is characterized by any of numbness, dysesthesia/parasthesia, tingling, and/or painless swelling or erythema of the distal extremities. Grade 2 is defined as painful erythema of the hands and/or feet and/or discomfort affecting the patient's activities of daily living. Grade 3 HFS is defined as moist desquamation, ulceration, and blistering or severe pain of the hands and/or feet and/or severe discomfort that causes the patient to be unable to work or perform activities of daily living.

HFS is progressive with dose and duration of exposure to fluoropyrimidines. The FDA-approved XELODA® product insert reports a 54%-67% incidence of HFS irrespective of grade during treatment with capecitabine at the FDA-approved dose, with a grade 3 incidence of 11-17%. HFS is also seen in treatment with other chemotherapeutic agents, including antimetabolites such as cytarabine, and agents of other classes, such as docetaxel and doxorubicin, including pegylated liposomal forms of doxorubicin (CAELYX®).

The pathophysiology of hand-foot syndrome is as yet unknown and variously ascribed to metabolites of 5-FU, local drug accumulation, increased levels of anabolic enzymes in the affected tissues, and various other factors. See, for example, Childress and Lokich, *Amer. J. Clinical Oncology* 26:435-436 (2003); Leo et al., *J. Chemother.* 6:423-426 (1994); Elasmar et al., *Jpn J. Clin. Oncol.* 31:172-174 (2001); and Fischel et al., "Experimental arguments for a better understanding of hand-foot syndrome under capecitabine," *Proc. Amer. Ass'n Cancer Res.* 45:487 (abstract #2119) (March 2004).

In the face of such mechanistic uncertainty, the current standard of practice is to cease or attenuate the dose of fluoropyrimidine when hand-foot syndrome develops. Unfortunately, the severity of hand-foot syndrome appears to correlate with tumor response, Chua et al., "Efficacy of capecitabine monotherapy in patients with recurrent and metastatic nasopharyngeal carcinoma pretreated with platinum-based chemotherapy," *Proc. Am. Soc. Clin. Oncol.* 22:511 (abstr. 2055) (2003); dose attenuation to reduce the symptoms of hand-foot syndrome thus also reduces efficacy of tumor treatment.

Topical treatment with DMSO, which has also been proposed, see U.S. Pat. No. 6,060,083, is not typically practiced in the clinic and is of uncertain efficacy.

While hand-foot syndrome is common during capecitabine treatment, it is rarely seen with the ftorafur-containing prodrug combinations UFT and S-1. S-1 lacks uracil yet, like UFT, causes hand-foot syndrome only rarely. The reason for the disparate prevalence is unknown, with the etiology of hand-foot syndrome with S-1 administration suggested to differ from that seen with capecitabine and/or 5-FU. Elasmar et al., *Jpn J. Clin. Oncol.* 31:172-174 (2001).

Systemically-administered chemotherapeutic agents other than fluoropyrimidine antimetabolites also cause side effects in various organs and tissues that are not involved in the disease being treated. Many of these agents interact with, and are metabolized by, complex metabolic pathways.

There is thus a need in the art for compositions and methods for preventing and/or treating side effects of systemically administered chemotherapeutic agents.

There is a further need in the art for methods and compositions for preventing and/or treating side effects of systemically administered chemotherapeutic agents that neither abrogate nor attenuate the therapeutic effect of the systemically administered agent, thus permitting such chemotherapeutic agents to be used at therapeutic dosage levels.

There is a particular need for methods and compositions for preventing and/or treating hand-foot syndrome, including methods and compositions that would obviate the withdrawal or attenuation of the dose of systemically administered chemotherapeutic agent, thus permitting systemically administered chemotherapeutic agents, such as fluoropyrimidines, to be administered at therapeutic dosage levels.

SUMMARY OF THE INVENTION

The present invention solves these and other needs in the art by providing methods, compositions, and kits for protecting desired organs, tissues, and/or cells (collectively hereinafter, "tissues") from the toxic effects of a systemically distributed toxic agent, such as a systemically administered chemical, biological, radiochemical, or radiobiological anticancer chemotherapeutic agent.

The method is based on the asymmetric delivery of the anticancer therapeutic agent and a tissue protectant to a subject, with the anticancer therapeutic agent delivered throughout the body, typically by systemic administration, and the protectant vectored, or targeted, to the tissue to be protected.

In a first set of embodiments, the protectant is administered so as to achieve high concentration at or within the tissue to be protected, with low to negligible systemic distribution. In a second set of embodiments, the protectant is administered so as to reduce the concentration of the anticancer therapeutic locally at or within the tissue to be protected. In both cases, the protectant can serve to restore normal homeostasis primarily, or exclusively, to the tissue to be protected.

In the first set of embodiments, the protectant is typically administered locally, local administration being effective to establish a concentration of the protectant agent at the desired tissue that is sufficient to protect the tissue from toxicity by the systemically distributed anticancer therapeutic agent. The route of administration is chosen or adapted so as additionally to constrain the circulating concentration of the protectant to levels that are insufficient to abrogate the clinical efficacy of the systemically distributed anticancer therapeutic agent or metabolite.

The spatial differential in concentration achieved in the methods of the present invention obviates the need to achieve a pharmacological distinction between the agents, such as a difference in affinity for one or more enzymes for which both agents serve as substrates. The methods thus permit two agents having near-identical pharmacokinetics and/or enzyme specificity or affinity to serve, respectively, as the toxic therapeutic agent and as the protectant.

The spatially directed administration of the protectant allows concentrations of the protectant to be used that might be deleterious or harmful if achieved systemically. The methods also permit an agent to be used as a protectant that would, if administered systemically, diminish or abrogate the clinical efficacy of the systemically distributed anticancer therapeutic agent.

In embodiments of the methods of the present invention in which the protectant agent is, in current clinical practice, coadministered with the toxic agent to achieve a systemic effect, the method comprises dissociating the routes of administration of the two agents, administering the toxic agent by means sufficient to achieve systemic distribution—such as by enteral or parenteral systemic administration—and administering the protectant agent in a spatially directed fashion.

The protectant itself can usefully be a substrate, often biologically active, for one or more enzymes involved in the metabolic activation of the systemically distributed toxic agent. The protectant, in other alternative embodiments, can physically reduce, remove or inactive the anticancer therapeutic at the tissue or organ to be protected.

Accordingly, in a first aspect, the invention provides a method of protecting a desired body tissue from toxic effects of one or more systemically distributed anticancer therapeutic agents or metabolites thereof. The method comprises targeting one or more protectant agents for nonsystemic delivery to the tissue desired to be protected.

In a first series of embodiments, targeted nonsystemic delivery comprises administering one or more protectant agents so as to establish a local concentration of the protectant agents in the tissue desired to be protected that is sufficient to protect the tissue from the toxic effects of the systemic agent. Administration is performed so as additionally to ensure that the circulating concentration of the protectant agents is insufficient to abrogate the clinical efficacy of the systemically distributed anticancer therapeutic agent or metabolite at a tissue desired to be treated.

In typical embodiments, the systemically distributed anticancer therapeutic agent, or a metabolite or precursor thereof, is systemically administered, for example by parenteral administration, such as by intravenous administration, or enteral administration, such as orally.

In these embodiments, typically the more protectant agents is administered locally to the desired tissue, such as by topical administration to an integumentary surface, such as skin.

The timing of administration of the protectant can vary.

In some embodiments, the one or more protectant agents is administered before the at-risk tissue manifests toxic effects from the systemically distributed anticancer therapeutic agent or metabolite thereof, at times even before systemic administration of the anticancer therapeutic agent (or metabolite or precursor thereof). In various embodiments, the one or more protectant agents is administered concurrently with systemic administration of the anticancer therapeutic agent. In some embodiments, the protectant is administered before, during, and after systemic administration of the anticancer therapeutic agent.

In the first series of embodiments of the methods of the present invention, the local concentration of each of the one or more protectant agents is at least about 5-fold greater than the circulating concentration of the protectant agent, often at least about 10-fold greater than the circulating concentration of said protectant agent, at times at least about 100-fold greater even at least about 1000-fold greater than that in the circulation.

In some embodiments, at least one of the at least one protectant agents inhibits in vivo activation of the systemically administered anticancer therapeutic agent or metabolite or precursor thereof, for example by inhibiting its anabolism. At least one of the at least one protectant agents can, for example, be a substrate for an enzyme involved in anabolic activation of the systemically administered anticancer therapeutic agent, or a metabolite or precursor thereof.

In other embodiments, at least one of the at least one protectant agents facilitates in vivo catabolism of the systemically administered anticancer therapeutic agent, or a metabolite or precursor thereof.

The anticancer therapeutic agent, metabolite or precursor thereof, can be an antimetabolite, such as a nucleotide, a nucleoside, or a derivative, analogue, or precursor thereof. For example, the systemically distributed (typically, systemically administered) anticancer therapeutic agent can be ara-C (cytarabine) or a fluoropyrimidine. The fluoropyrimidine can be parenterally administrable fluoropyrimidines and/or orally administrable.

In some embodiments, the fluoropyrimidine is 5-FU or a 5-FU prodrug such as ftorafur, doxifluridine, and capecitabine. The systemically administered fluoropyrimidine or fluoropyrimidine prodrug can be composited with an inhibitor of dihydropyrimidine dehydrogenase (DPD). Among such compositions is a composition comprising ftorafur, 5-chloro-2,4-dihydroxypyridine, and oxonic acid.

In other embodiments, the systemically distributed (typically, systemically administered) anticancer therapeutic agent, or metabolite or precursor thereof, can be an anthracycline, or a topoisomerase I inhibitor, or an antagonist of EGF or VEGF. For example, the systemically distributed agent can be an anthracycline selected from the group consisting of doxorubicin, nonpegylated liposomal doxorubicin, pegylated liposomal doxorubicin, daunorubicin, liposomal daunorubicin, epirubicin, and idarubicin.

The systemically distributed (typically, systemically administered) anticancer therapeutic agent can be associated with toxicity to an epithelium, such as an integumentary or mucosal epithelium.

In certain embodiments, the toxicity is hand-foot syndrome. In these embodiments, the protectant is usefully administered topically to the palmar and/or plantar skin surface. In embodiments in which hand-foot syndrome is caused by systemic administration of a fluoropyrimidine, such as 5-FU or capecitabine, at least one of said at least one protectant agents is usefully uracil, usefully composited in a hydrophilic ointment for topical administration to the skin of the hands and feet.

In a second series of embodiments of the methods of the present invention, the targeted nonsystemic delivery of protectants comprises administering the protectant agent so as to effect a reduction, in the tissue desired to be protected, in the concentration of the systemically distributed anticancer therapeutic agent (or metabolite thereof) that is sufficient to protect the tissue from the toxic effects of the systemic agent. The circulating concentration of the protectant agents is insufficient to abrogate the clinical efficacy of the systemically distributed anticancer therapeutic agent or metabolite at a tissue desired to be treated.

The methods of the present invention can sufficiently protect the at-risk tissue as to permit the full, unattenuated dose of anticancer therapeutic agent to be administered, with neither dose interruption, cessation, nor attenuation.

Thus, in a second aspect, the invention provides a method of treating neoplasia.

The method comprises: systemically administering an anticancer therapeutic agent, or a precursor or metabolite thereof, to a subject in need thereof; and concurrently targeting one or more protectant agents for nonsystemic delivery to the tissue desired to be protected by any of the methods above-described.

For example, the method can comprise the concurrent administration of one or more protectant agents so as to establish a local concentration of the protectant agents in the tissue desired to be protected that is sufficient to protect the tissue from the toxic effects of the systemic agent. Administration is performed so as additionally to ensure that the circulating concentration of the protectant agents is insufficient to abrogate the clinical efficacy of the systemically distributed anticancer therapeutic agent or metabolite at a tissue desired to be treated.

In other embodiments, the method can comprise the concurrent administration of one or more protectant agents so as to effect a reduction, in the tissue desired to be protected, in the concentration of the systemically distributed anticancer therapeutic agent (or metabolite thereof) that is sufficient to protect the tissue from the toxic effects of the systemic agent. The circulating concentration of the protectant agents is insufficient to abrogate the clinical efficacy of the systemically distributed anticancer therapeutic agent or metabolite at a tissue desired to be treated.

The systemically administered anticancer therapeutic agent, precursor or metabolite thereof can be an antimetabolite, such a fluoropyrimidine, including parenterally administrable and orally administrable fluoropyrimidines, such as 5-FU, ftorafur, Carmofur, capecitabine, doxifluridine, UFT, S-1, or Emitefur.

In such embodiments, at least one of the at least one protectant agents concurrently administered with the fluoropyrimidine can be uracil. The uracil can, for example, be administered topically to the plantar and/or palmar skin surfaces.

In another aspect, the invention provides pharmaceutical compositions for local application to a body tissue, the composition capable of establishing a local concentration of one or more protectant agents sufficient to protect the tissue from toxic effects of one or more systemically distributed anticancer therapeutic agents or metabolites thereof without abrogating the clinical efficacy of said systemically distributed anticancer therapeutic agent or metabolite. The composition comprises at least one protectant agent; and a pharmaceutically acceptable carrier suitable for local application.

In some embodiments, at least one of the at least one protectants in the composition is uracil. Uracil can be present within the composition at a concentration by weight of at least about 0.01%, often at least about 0.1%, even at least about 1.0%. In various embodiments, uracil can be present within at a concentration by weight of no more than about 60%, often at a concentration of no more than about 5%.

In yet a further aspect, the invention provides kits for oral delivery of an anticancer therapeutic agent or precursor ("prodrug") thereof with reduced toxicity to a desired tissue.

The kit comprises at least one dose of an orally administrable anticancer therapeutic agent or precursor thereof; and at least one dose of a locally administrable tissue protectant composition. In some embodiments, the orally administrable anticancer therapeutic agent or precursor is a fluoropyrimidine or fluoropyrimidine composition, such as ftorafur, Carmofur, capecitabine, doxifluridine, UFT, S-1, or Emitefur.

In presently preferred kits, the fluoropyrimidine is capecitabine, the protectant composition is suitable for topical delivery to the skin, and the protectant composition comprises uracil. The uracil can usefully be present at a concentration by weight of at least about 0.1%, even at least about 1.0%. The uracil can be present within the composition at a concentration by weight of no more than about 60%, even no more than about 10%, with uracil usefully present in a weight percentage of about 0.11%-10%, even 1%-5%.

BRIEF DESCRIPTION OF THE DRAWINGS

The above and other objects and advantages of the present invention will be apparent upon consideration of the following detailed description taken in conjunction with the accompanying drawings, in which like characters refer to like parts throughout, and in which.

DETAILED DESCRIPTION

Figure 1:
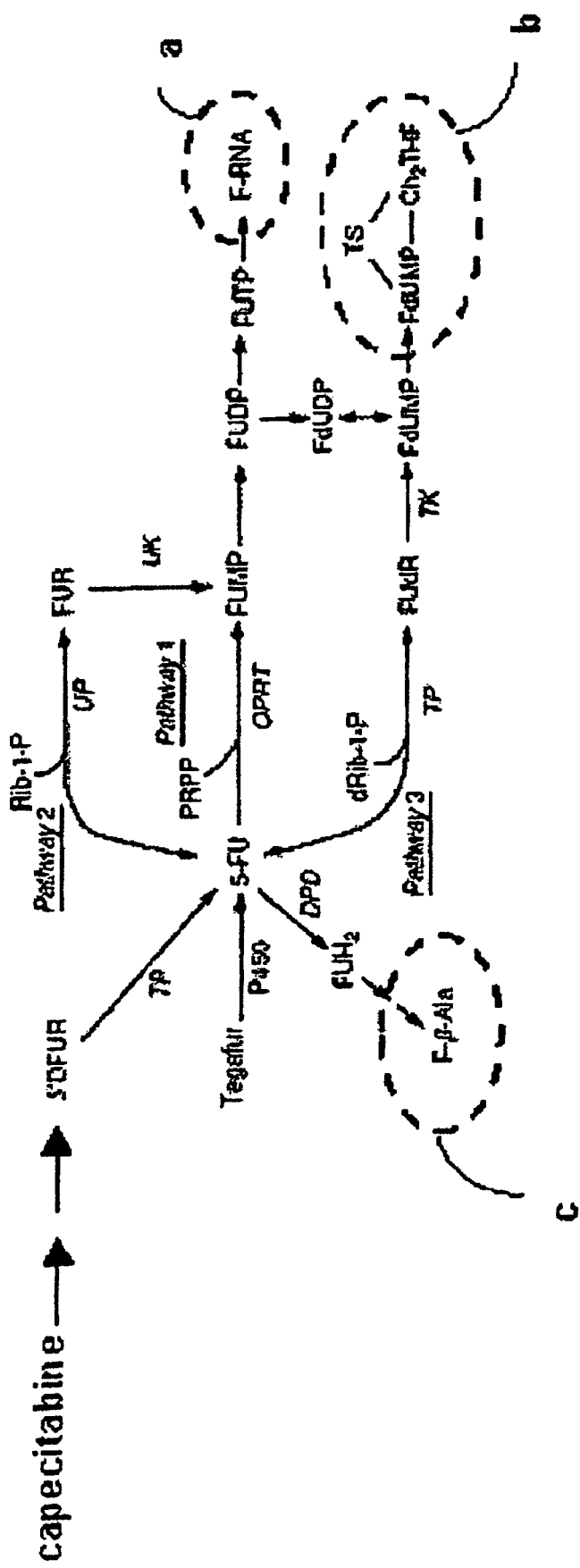
FIG. 1 shows the basic metabolic pathways for anabolic activation and catabolic degradation of fluoropyrimidines, as known in the art.

In a first aspect, the invention provides a method of protecting a desired organ or body tissue from toxic effects of one or more toxic agent, such as anticancer therapeutic agents, or metabolites thereof, that are systemically distributed through the body of a subject, typically a human patient undergoing chemotherapy for cancer.

The body tissue desired to be protected may be any body tissue that is not intended to be treated by the systemically distributed anticancer therapeutic agent or anticancer therapeutic agent metabolite.

For example, in embodiments in which the patient is being treated for cancer, the body tissue desired to be protected would typically be one that does not contain neoplastic cells. Analogously, in embodiments in which the patient is being treated with an anticancer therapeutic agent (or anticancer therapeutic agent metabolite) to effect myeloablation, for example to condition the patient prior to bone marrow transplantation, the tissue desired to be protected may be any tissue other than the bone marrow.

The method comprises administering one or more protectant agents to the subject.

In a first series of embodiments, the one or more protectant agents are so administered as to establish a local concentration of protectant agent in the organ, tissue, or cells (hereinafter, collectively "tissue") desired to be protected that is sufficient to protect the tissue from the toxic effects of the systemically distributed toxic agent, such as a systemically distributed anticancer therapeutic agent or anticancer therapeutic agent metabolite, yet also constrain the circulating concentration of protectant to levels that are insufficient to abrogate the clinical efficacy of the systemically distributed anticancer therapeutic agent or metabolite.

In a second series of embodiments, the one or more protectant agents are so administered as to lower the active concentration of the systemically distributed toxic agent (such as a systemically distributed anticancer therapeutic agent, or metabolite thereof) at or within the tissue desired to be protected to a level that protects the tissue from the toxic effects of the systemically distributed toxic agent, without, however, lowering the levels of the systemically distributed toxic agent, at the tissue desired to be treated, to levels that abrogate the clinical efficacy of the systemically distributed anticancer therapeutic agent or metabolite.

"Protection" intends a clinically observable decrease in one or more toxic effects in the body tissue desired to be protected, as compared to the toxic effects that would be seen absent the protectant.

Protection can be total, preventing all symptoms of toxicity in the desired tissue; protection can be partial, reducing and/or delaying development of all or a subset of symptoms of toxicity in the desired tissue. In some embodiments, protection is sufficient to permit administration of the full dose and course of intended therapy with anticancer therapeutic agent or metabolite or precursor (prodrug) without dose cessation, dose attenuation, and/or alteration in dosage schedule. In some embodiments, protection is sufficient to allow an increase in dose of the anticancer therapeutic agent or metabolite or precursor.

The circulating concentration of the one or more protectants is constrained to levels that are insufficient to abrogate the clinical efficacy of the systemically distributed anticancer therapeutic agent or metabolite thereof.

"Abrogate" intends a diminution in efficacy of the anticancer therapeutic agent (or metabolite thereof) at the tissue desired to be treated that is sufficiently great as to render therapy with the anticancer therapeutic agent or anticancer therapeutic agent metabolite clinically ineffective or clinically inadvisable. In some embodiments, the circulating concentration of the one or more protectant agents is sufficiently low as to cause no clinically observable diminution in potency or efficacy of the systemically distributed anticancer therapeutic agent (or metabolite thereof) at the tissue desired to be treated, such as a tissue having neoplastic cells. In other embodiments, the circulating concentration of the one or more protectant agents causes a clinically observable diminution in potency or efficacy of the systemically distributed anticancer therapeutic agent (or metabolite) at the tissue desired to be treated, but is insufficient to abrogate the clinical efficacy of the systemically distributed anticancer therapeutic agent or metabolite thereof.

In typical embodiments, the local concentration of the one or more protectants in the tissue desired to protected from toxic effects will be greater than the concentration in the circulation. In some embodiments, the circulating concentration of the one or more protectants will be greater, in turn, than their concentration in the tissues desired to be treated with the systemically distributed anticancer therapeutic agent (such as a cancerous tissue).

In some embodiments, the local concentration of each of the one or more protectant agents in the tissue desired to be protected is at least 5-fold greater than the circulating concentration of the protectant agent. In other embodiments, the local concentration is at least 10-fold, at least 20-fold, at least 30-fold, at least 40-fold, at least 50-fold or more greater than the concentration of the protectant in the circulation. In various embodiments, the local concentration can be as high as at least 60-fold, 70-fold, 80-fold, 90-fold, even as high as 100-fold or more greater than the concentration of the protectant in the circulation. In some embodiments, the local concentration of protectant can be as high as 1000-fold higher than in the circulation, or even more.

In various embodiments, the local concentration of protectant in the tissue desired to be protected is at least 10-fold, at least 20-fold, at least 30-fold, at least 40-fold, at least 50-fold or more greater than the concentration of the protectant in the tissue desired to be treated. In various embodiments, the local concentration in the tissue desired to be protected can be as high as at least 60-fold, 70-fold, 80-fold, 90-fold, even as high as 100-fold or more greater than the concentration of the protectant in the tissue desired to be treated. In some embodiments, the local concentration of protectant can be as high as 1000-fold higher than in the tissue desired to be treated, or even more. The tissue desired to be treated can, e.g., be a tumor within a body tissue or the entirety of a body tissue within which a portion of the cells are neoplastic.

Typically, the anticancer therapeutic agent or metabolite becomes systemically distributed upon or following systemic administration of the anticancer therapeutic agent, its metabolite, or a precursor thereof to the patient.

The anticancer therapeutic agent (or metabolite) can be a chemical agent, a biological agent, a radiochemical agent or a radiobiological agent that has antineoplastic activity.

In some embodiments, the anticancer therapeutic agent, metabolite thereof, or precursor thereof is administered parenterally, such as by intravenous infusion, either continuous or bolus infusion, by intramuscular injection, by subcutaneous injection, or by intrathecal administration. In other embodiments, the anticancer therapeutic agent, metabolite thereof, or precursor thereof is administered orally. In yet other embodiments, the anticancer therapeutic agent, metabolite, or precursor is administered by transepithelial means, as by anal or vaginal suppository. In yet other embodiments, the anticancer therapeutic agent, metabolite, or precursor is implanted into the patient.

The systemically distributed anticancer therapeutic agent or metabolite can be an antimetabolite, such as a nucleotide, a nucleoside, or a derivative, analogue, or precursor thereof. For example, in certain embodiments, the systemically distributed anticancer therapeutic agent can be a purine antimetabolite such as mercaptopurine, azathioprine, thioguanine, or fludarabine. In other embodiments, the systemically distributed anticancer therapeutic agent can be a pyrimidine antimetabolite such as ara-C (cytarabine), gemcitabine, azacitidine, or a fluoropyrimidine, or a metabolite thereof.

In some of these embodiments, the systemically distributed anticancer therapeutic agent is a fluoropyrimidine.

In certain of these embodiments, the fluoropyrimidine is a parenterally administrable fluoropyrimidine, such as 5-FU. In other embodiments, the fluoropyrimidine is an orally administrable fluoropyrimidine, such as capecitabine, doxifluridine, or tegafur, alone or formulated in admixture with one or more inhibitors of dihydropyrimidine dehydrogenase (DPD). In certain embodiments, for example, the fluoropyrimidine (such as tegafur) can be administered in a composition that further comprises uracil and/or 5-chloro-2,4-dihydroxypyridine, and optionally oxonic acid.

In other embodiments, the anticancer therapeutic agent is an anthracycline, or precursor or metabolite thereof. In some of these embodiments, the anticancer therapeutic agent can be selected from the group consisting of doxorubicin, nonpegylated liposomal doxorubicin, pegylated liposomal doxorubicin, daunorubicin, liposomal daunorubicin, epirubicin, and idarubicin.

In other embodiments, the anticancer therapeutic agent can be a taxane, such as docetaxel or paclitaxel.

In typical embodiments, the one or more protectant agents is administered locally to the tissue desired to be protected. In some such embodiments, the one or more protectant agents is administered topically to the tissue desired to be protected. In other such embodiments, the one or more protectant agents is administered by local injection, such as by local injection of a depotized form of the one or more protectant agents.

In some embodiments of the methods of the present invention, the one or more protectant agents is administered before the tissue desired to be protected manifests toxic effects of the systemically distributed anticancer therapeutic agent or metabolite thereof.

Often, this prophylactic or preventative administration of the one or more protestant agents is preferred. Such timing is particularly preferred in embodiments in which the one or more protectant agents is to be administered to the skin as the tissue desired to be protected—e.g. to prevent, ameliorate, delay, or treat hand-foot syndrome—because toxic side effects, once manifested in the skin, can increase its permeability to, or otherwise increase its absorption of, the protectant, potentially increasing the circulating concentration of the protectant agent.

In certain of these embodiments, the one or more protectant agents is administered before systemic administration of the anticancer therapeutic agent, metabolite thereof, or precursor thereof. In certain embodiments, the one or more protectant agents is administered concurrently with systemic administration of the anticancer therapeutic agent, metabolite thereof, or precursor thereof. In some embodiments, the one or more protectant agents is administered before and during systemic administration of the anticancer therapeutic agent, metabolite thereof, or precursor thereof. In yet other embodiments, the one or more protectant agents is optionally administered for a period following cessation of systemic administration of the one or more anticancer therapeutic agents, or precursors, or metabolites thereof.

The protectant agent can, in some embodiments, be one that inhibits in vivo activation of the systemically administered anticancer therapeutic agent, metabolite or precursor thereof.

For example, the protectant can in some embodiments inhibit anabolic activation of a systemically administered anticancer therapeutic agent, metabolite, or precursor thereof. In some embodiments, the protectant agent can be a substrate, such as a competitive substrate, of an enzyme involved in anabolic activation of a systemically administered anticancer therapeutic agent or metabolite or precursor thereof. In embodiments in which the protectant acts as a substrate for an enzyme, the protectant agent can be a naturally-occurring compound.

In embodiments in which the systemically distributed anticancer therapeutic agent is a fluoropyrimidine, for example, the protectant agent can be a substrate, such as a competitive substrate, of an enzyme involved in anabolic activation of the systemically administered fluoropyrimidine, such as a substrate for thymidine phosphorylase (TP), and/or uridine phosphorylase (UP), and/or orotate phosphoribosyl transferase (OPRT).

The protectant can, for example, be a naturally occurring compound, such as a compound that serves as a substrate for any one or more of TP, UP, and OPT. The compound can be a naturally occurring nitrogenous base, such as a pyrimidine, including uracil. In other embodiments, the compound can be a non-naturally occurring nitrogenous base, such as a non-naturally occurring pyrimidine.

Typically, the protectant will not act as an irreversible inhibitor of—or otherwise interfere with—an enzymatic activity or pathway in the cell, and thus will not occasion an imbalance in the absolute and relative nucleotide concentrations within the cell.

In other embodiments, the protectant agent can be one that facilitates in vivo catabolism of the systemically administered anticancer therapeutic agent, metabolite, or precursor thereof.

In embodiments in which the systemically distributed anticancer therapeutic agent is a fluoropyrimidine, for example, the protectant agent can act to increase the amount or activity of dihydropyrimidine dehydrogenase (DPD) in the tissue desired to be protected.

For example, the protectant agent can include nucleic acids capable of expressing a protein, such as DPD, and can be administered, for example, by injection, as described, for example, in U.S. Pat. Nos. 5,580,859 and 6,706,694, incorporated herein by reference in its entirety.

The protectant agent may be administered using a variety of dosage schedules designed to establish and maintain a local concentration in the tissue desired to be protected that is sufficient to protect the tissue from the toxic effects of the systemically distributed anticancer therapeutic agent or anticancer therapeutic agent metabolite, yet constrain the circulating concentration of protectant to levels that are insufficient to abrogate the clinical efficacy of the systemically distributed anticancer therapeutic agent or metabolite.

The exact dosage schedule will depend, inter alia, on any one or more of the identity of the systemically distributed chemotherapeutic agent or metabolite, the circulating concentration of chemotherapeutic agent or metabolite, the tissue desired to be protected, the severity of side effects desired to be prevented or treated, and the formulation of the protectant composition, particularly its concentration in the protectant composition; determination of the proper dosage schedule of protectant agent is within the skill of the clinical artisan.

For example, in embodiments of the methods of the present invention in which the protectant agent is administered topically to skin in an ointment composition, the protectant can usefully be administered once a day, twice a day, three times a day, four times a day, or more times a day. As would be understood in the art, the composition can be applied with different dosage schedules to different tissues of a single patient. For example, the composition may be applied twice a day to the plantar surface of the feet, but applied more frequently to the hands, such as after each washing of the hands. The exact schedule may vary by patient.

In some embodiments, the amount of protectant administered per dose is at least 0.01 g, 0.02 g, 0.03 g, 0.04 g, 0.05 g, 0.06 g, 0.07 g, 0.08 g, 0.09 g, 0.1 g, 0.2 g, 0.3 g, 0.4 g, 0.5 g, 0.6 g, 0.7 g, 0.8 g, 0.9 g, 1.0 g, 1.5 g, 2.0 g, 2.5 g, 3 g, 4 g, even 5 g or more, with intermediate values permissible. Typically, the amount of protectant administered per dose is no more than about 10 g, 9 g, 8 g, 7 g, 6 g, even no more than about 5 g, 4.5 g, 4 g, 3.5 g, 3 g, 2 g, 1 g, and in certain embodiments even no more than about 0.5 g, 0.4 g, 0.3 g, 0.2 g, even no more than about 0.1 g.

For example, in embodiments of the methods of the present invention in which uracil as the protectant agent is administered two to four times per day to the palmar and/or plantar surfaces of a patient undergoing systemic administration of an anticancer therapeutic agent, prodrug or metabolite thereof, such as systemic administration of a fluoropyrimidine, such as 5-FU or capecitabine, the amount of uracil administered per dose can usefully be at least about 0.01 g, 0.02 g, 0.03 g, 0.04 g, 0.05 g, 0.06 g, 0.07 g, 0.08 g, 0.09 g, 0.1 g, 0.2 g, 0.3 g, 0.4 g, 0.5 g, 0.6 g, 0.7 g, 0.8 g, 0.9 g, even at least 1.0 g, and typically no more than about 2.0 g, 1.5 g, 1.0 g, 0.9 g, 0.8 g, 0.7 g, 0.6 g, 0.5 g, 0.4 g, 0.3 g, 0.2 g, with a dose of 0.1 g currently preferred.

In another aspect, the invention provides protectant agents formulated in compositions that permit local concentrations of protectant to be established that are sufficient to protect the tissue from the toxic effects of the systemically distributed anticancer therapeutic agent or anticancer therapeutic agent metabolite, yet constrain the circulating concentration of protectant to levels that are insufficient to abrogate the clinical efficacy of the systemically distributed anticancer therapeutic agent or metabolite.

Compositions of the present invention comprise one or more protectant agents and at least one pharmaceutically acceptable carrier or excipient.

Each of the at least one protectant agents is typically present in the protectant composition to a weight/weight percentage of at least 0.01%, 0.05%, 1.0%, 1.5%, 2.0%, 2.5%, 3.5%, 4.0%, 4.5%, 5.0%, 10%, 15%, 20%, 25%, 30%, 35%, 40%, 45%, 50%, 55%, 60%, 65%, 70%, 75%, even 80% or more, with intermediate values permissible, and is typically present to a weight/weight percentage of no more than about 80%, 75%, 70%, 65%, 60%, 55%, 50%, 45%, 40%, 35%, 30%, 25%, 20%, 15%, 10%, 5%, 4.5%, 4.0%, 3.5%, 3.0%, 2.5%, 2.0%, 1.5%, 1.0%, and even, at times, to a weight/weight percentage of no more than about 0.05%, even as little as 0.01%.

In embodiments of the compositions of the present invention comprising a plurality of protectant agents, typically the plurality of protectants are cumulatively present to a weight/weight percentage of at least 0.01%, 0.05%, 1.0%, 1.5%, 2.0%, 2.5%, 3.5%, 4.0%, 4.5%, 5.0%, 10%, 15%, 20%, 25%, 30%, 35%, 40%, 45%, 50%, 55%, 60%, 65%, 70%, 75%, even 80% or more, with intermediate values permissible, and is typically present to a weight/weight percentage of no more than about 80%, 75%, 70%, 65%, 60%, 55%, 50%, 45%, 40%, 35%, 30%, 25%, 20%, 15%, 10%, 5%, 4.5%, 4.0%, 3.5%, 3.0%, 2.5%, 2.0%, 1.5%, 1.0%, 0.05%, even as little as 0.01%, with intermediate values permissible.

In embodiments that are presently preferred for protecting the palmar and/or plantar skin surfaces from hand-foot syndrome, such as during systemic administration of a fluoropyrimidine, an anthracycline, or a taxane anticancer therapeutic agent, or metabolite or precursor thereof, the compositions of the present invention typically comprise uracil as the protectant agent, with the composition comprising uracil to a weight/weight percentage of at least 0.01%, 0.05%, 1.0%, 1.5%, 2.0%, 2.5%, 3.5%, 4.0%, 4.5%, 5.0%, 10%, 15%, 20%, 25%, 30%, 35%, 40%, 45%, 50%, 55%, 60%, 65%, 70%, 75%, even 80% or more, with intermediate values permissible; in such compositions, uracil is typically present to a weight/weight percentage of no more than about 80%, 75%, 70%, 65%, 60%, 55%, 50%, 45%, 40%, 35%, 30%, 25%, 20%, 15%, 10%; 5%, 4.5%, 4.0%, 3.5%, 3.0%, 2.5%, 2.0%, 1.5%, 1.0%, and even, at times, to a weight/weight percentage of no more than about 0.05%, even as little as 0.01%, with intermediate values permissible.

In presently preferred compositions for protecting the palmar and/or plantar skin surfaces, uracil is present to a weight/weight percentage of at least about 0.1%, 0.2%, 0.3%, 0.4%, 0.5%, 0.6%, 0.7%, 0.8%, 0.9%, even to a weight/weight percentage of at least about 1.0%, 1.1%, 1.2%, 1.3%, 1.4%, 1.5%, 1.6%, 1.7%, 1.8%, 1.9%, 2.0%, 2.5%, 3.0% or more, with intermediate values permissible. In some embodiments, uracil is present to a weight/weight percentage of at least about 3.5%, 4.0%, 4.5%, 5.0%, 10%, 15%, 20%, 25%, 30%, 35%, 40%, 45%, 50%, 55%, even at least about 60%, typically no more than about 60%, 55%, 50%, 45%, 40%, 35%, 30%, 25%, 20%, 15%, 10%, 5%, 4.5%, 4.0%, 3.5%, 3.0%, 2.5%, 2.0%, 1.5%, 1.0%, 0.05%, with intermediate values permissible. In certain useful embodiments, uracil is present to a weight/weight percentage of about 1%.

The exact formulation of the protectant agent compositions of the present invention will depend upon the identity of the tissue desired to be protected. Pharmaceutical formulation is a well-established art, and is further described in Gennaro (ed.), *Remington: The Science and Practice of Pharmacy*, 20th ed., Lippincott, Williams & Wilkins (2000), (ISBN: 0683306472); Ansel et al., *Pharmaceutical Dosage Forms and Drug Delivery Systems*, 7th ed., Lippincott Williams & Wilkins Publishers (1999) (ISBN: 0683305727); and Kibbe (ed.), *Handbook of Pharmaceutical Excipients American Pharmaceutical Association*, 3rd ed. (2000) (ISBN: 091733096X), the disclosures of which are incorporated herein by reference in their entireties.

In embodiments in which the tissue desired to be protected is the skin, for example, the one or more protectant agents will typically be formulated for localized, typically topical, administration to the skin surface. In embodiments in which the patient is being treated systemically with a fluoropyrimidine, an anthracycline, or a taxane anticancer therapeutic agent, or precursor or metabolite thereof, for example, the one or more protectant agents will often be formulated for topical administration to the palmar and plantar skin surfaces.

Compositions of the present invention intended for topical administration to the skin may, for example, be anhydrous, aqueous, or water-in-oil or oil-in-water emulsions. Emulsions are presently preferred. Compositions of the present invention may further include one or more pharmaceutically acceptable carriers or excipients and various skin actives. Amounts of the carrier may range from about 1 to about 99%, preferably from about 5 to about 70%, optimally from about 10 to about 40% by weight. Among useful carriers are emollients, water, inorganic powders, foaming agents, emulsifiers, fatty alcohols, fatty acids, and combinations thereof.

Emollients can be selected from polyols, esters and hydrocarbons.

Polyols suitable for the invention may include propylene glycol, dipropylene glycol, polypropylene glycol, polyethylene glycol, sorbitol, hydroxypropyl sorbitol, hexylene glycol, 1,3-butylene glycol, 1,2,6-hexanetriol, glycerin, ethoxylated glycerin, propoxylated glycerin, xylitol and mixtures thereof.

Esters useful as emollients include alkyl esters of fatty acids having 10 to 20 carbon atoms. Methyl, isopropyl, and butyl esters of fatty acids are useful herein. Examples include hexyl laurate, isohexyl laurate, isohexyl palmitate, isopropyl palmitate, decyl oleate, isodecyl oleate, hexadecyl stearate, decyl stearate, isopropyl isostearate, diisopropyl adipate, diisohexyl adipate, dihexyldecyl adipate, diisopropyl sebacate, lauryl lactate, myristyl lactate, and cetyl lactate. Particularly preferred are C12-C15 alcohol benzoate esters.

Esters useful as emollients also include alkenyl esters of fatty acids having 10 to 20 carbon atoms. Examples thereof include oleyl myristate, oleyl stearate and oleyl oleate.

Esters useful as emollients also include ether-esters such as fatty acids esters of ethoxylated fatty alcohols.

Esters useful as emollients also include polyhydric alcohol esters. Ethylene glycol mono and di-fatty acid esters, diethylene glycol mono- and di-fatty acid esters, polyethylene glycol (200-6000) mono- and di-fatty acid esters, polyglycerol poly-fatty esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.

Esters useful as emollients additionally include wax esters such as beeswax, spermaceti, myristyl myristate, stearyl stearate.

Esters useful as emollients still further include sterol esters, of which cholesterol fatty acid esters are examples thereof.

Illustrative hydrocarbon carriers are mineral oil, polyalphaolefins, petrolatum, isoparaffin, polybutenes and mixtures thereof.

Inorganic powders are also useful as carriers in the compositions of the present invention. Examples include clays (such as Montmorillonite, Hectorite, Laponite and Bentonite), talc, mica, silica, alumina, zeolites, sodium sulfate, sodium bicarbonate, sodium carbonate, calcium sulfate and mixtures thereof.

The compositions of the present invention can also include aerosol propellants, serving as, or in addition to, carriers or excipients. Propellants can be based on volatile hydrocarbons such as propane, butane, isobutene, pentane, isopropane and mixtures thereof. Philips Petroleum Company is a source of such propellants under trademarks including A31, A32, A51 and A70. Halocarbons including fluorocarbons are further widely employed propellants.

The compositions of the present invention, particularly embodiments formulated for administration to the skin, can comprise emulsifiers, either serving as, or in addition to, carriers or excipients.

Emulsifiers may be selected from nonionic, anionic, cationic, or amphoteric emulsifying agents. They may range in amount anywhere from about 0.1 to about 20% by weight.

Illustrative nonionic emulsifiers are alkoxylated compounds based on C10-C22 fatty alcohols and acids and sorbitan. These materials are available, for instance, from the Shell Chemical Company under the Neodol trademark. Copolymers of polyoxypropylenepolyoxyethylene sold by the BASF Corporation under the Pluronic trademark are sometimes also useful. Alkyl polyglycosides available from the Henkel Corporation may also be utilized for purposes of this invention.

Anionic type emulsifiers include fatty acid soaps, sodium lauryl sulfate, sodium lauryl ether sulfate, alkyl benzene sulphonate, mono- and di-alkyl acid phosphates, sarcosinates, taurates and sodium fatty acyl isethionate.

Amphoteric emulsifiers useful in the compositions of the present invention include such materials as dialkylamine oxide and various types of betaines (such as cocamidopropyl betaine).

The compositions of the present invention can also include preservatives, such as methyl paraben and propyl paraben are useful to prevent microbial contamination.

In embodiments of the compositions of the present invention formulated for topical application to skin, the composition can usefully be formulated as an ointment, a cream, a lotion, a paste, an aerosol spray, a roll-on liquid, stick, or pad, or an aerosol foam (mousse) composition.

For example, mousse compositions of the present invention can be quick-breaking or slow-breaking foams, such as those described in U.S. Pat. Nos. 6,730,288, 6,627,585, 6,589,518, 6,395,258, 6,383,472, 6,113,888, 6,113,881, 6,080,392, 5,783,202, the disclosures of which are incorporated herein by reference in their entireties.

In one embodiment, the composition is a hydrophilic ointment comprising uracil as the protectant agent, and further comprising methyl paraben, propyl paraben, sodium lauryl sulfate, propylene glycol, sterol alcohol, white petrolatum, water and light mineral oil.

In embodiments in which the tissue desired to be protected is the mucosal epithelium of the mouth, as in chemotherapy-induced stomatitis, the protectant agents can be applied to the oral cavity in the form of a topical formulation. In methods of the present invention for protecting mucosal epithelium from the toxic effects of a systemically distributed anticancer therapeutic agent or metabolite thereof, care is typically taken to prevent or to reduce oral ingestion.

Formulations suitable for topical oral application include oral emulsions, magmas, gels, swishes, lozenges, pastes, creams, oral solutions, gums, etc., as are well known in the art. Any of these topical oral vehicles can be used in conjunction with the methods of the invention. Exact formulations, as well as methods of their preparation, will be apparent to those of skill in the art.

In one embodiment of a composition of the present invention useful for topical delivery to the mucosal epithelium of the mouth, the one or more protectant agents are administered in a topical gel-like formulation comprising a gel-like vehicle. The gel-like vehicle generally comprises a water-soluble gelling agent, a humectant and water, and has a viscosity of about 500 to 100,000 cps, preferably about 10,000 to 50,000 cps, more preferably about 15,000 to 30,000 cps and most preferably about 20,000 to 25,000 cps as measured with a Brookfield viscometer at about 25° C. The gelling agent provides the formulation with good mucoadhesion properties; the humectant with good moisturizing and moisture-barrier properties.

Gelling agents suitable for use with the vehicle of the invention include, e.g., agar, bentonite, carbomer (e.g., carbopol), water soluble cellulosic polymers (e.g., carboxyalkyl cellulose, hydroxyalkyl cellulose, alkyl cellulose, hydroxyalkyl alkylcellulose), povidone, kaolin, tragacanth and vee-gum, with hydroxylalkyl alkyl celluloses such as hydroxypropyl methylcellulose being preferred.

Humectants suitable for use with the gel-like vehicle of the invention include, e.g., glycerin, propylene glycol and sorbitol, with sorbitol being preferred.

Generally, the vehicle comprises about 0.1% (w/w) to 10% (w/w) water-soluble gelling agent, with about 0.25% (w/w) to 5% (w/w) being preferred and about 0.5% (w/w) to 3% (w/w) being most preferred and about 0.1% (w/w) to 20% (w/w) humectant. However, as the viscosity of the gel-like vehicle is of considerable importance, it will be understood that the above concentration ranges are for guidance only. The actual concentration of gelling agent will depend, in part, on the polymer selected, the supplier and the specific lot number. The actual concentrations of other ingredients will likewise affect the viscosity of the gel-like formulation. Choosing appropriate concentrations to yield a gel-like formulation with the desirable viscosity and other properties described herein is within the capabilities of ordinarily skilled artisans.

Additionally, the gel-like vehicle of the invention may include antimicrobial preservatives. Antimicrobial preservatives useful with the compositions of the invention include, but are not limited to, antifungal preservatives such as benzoic acid, alkylparabens, sodium benzoate and sodium propionate; and antimicrobial preservatives such as benzalkonium chloride, benzethonium chloride, benzyl alcohol, cetylpyridinium chloride, chlorobutanol, phenol, phenylethyl alcohol, phenylmercuric nitrate and thimerosal, with alkylparabens such as methylparaben, propylparaben and mixtures thereof being preferred.

An amount of antimicrobial preservative(s) effective for use with the formulations of the invention will be apparent to those of skill in the art and will depend, in part, on the antimicrobial agent(s) used. Typical concentrations range from about 0.01% (w/w) to about 2% (w/w).

The composition of the invention formulated for topical administration to the oral mucosa may also contain from about 1% (w/w) to 10% (w/w) of a sweetening agent such as aspartame, dextrose, glycerin, malitol, mannitol, saccharin sodium, sorbitol, sucrose and xylitol. Such sweetening agents are believed to aid patient compliance.

The pH of the composition will depend on the tissue protectant(s) contained in the composition. Determination of an optimal pH for stability and efficacy is well within the skill of the ordinary artisan.

Other optional ingredients that can be used without deleteriously affecting, and in some cases even enhancing, the efficacy of the formulations of the invention adapted for mucosal, notably oral mucosal, delivery, include, but are not limited to, acidifying agents such as acetic acid, citric acid, fumaric acid, hydrochloric acid, lactic acid and nitric acid; alkalinizing agents such as ammonia solution, ammonium carbonate, diethanolamine, monoethanolamine, potassium hydroxide, sodium borate, sodium carbonate, sodium hydroxide, triethanolamine and trolamine; buffering agents such as potassium metaphosphate, potassium phosphate, sodium acetate and sodium citrate; antioxidants such as ascorbic acid, ascorbyl palmitate, butylated hydroxyanisole, butylated hydroxytoluene, hypophosphorous acid, monothioglyceride, propyl gallate, sodium ascorbate, sodium bisulfite, sodium formaldehyde sulfoxylate and sodium metabisulfite; chelating agents such as edetate disodium and edetic acid; colorants such as FD&C Red No. 3, FD&C Red No. 20, FD&C Yellow No. 6, FD&C Blue No. 2, D&C Green No. 5, D&C Orange No. 5, caramel and ferric oxide, red; and flavoring agents such as anise oil, cinnamon oil, cocoa, menthol, orange oil, peppermint oil vanillin. Suitable concentrations for use will be apparent to those of skill in then art. Other optional ingredients, as well as suitable concentrations for use, can be found, for example, in Gennaro (ed.), *Remington: The Science and Practice of Pharmacy,* 20th ed., Lippincott, Williams & Wilkins (2000) (ISBN: 0683306472).

In embodiments of the methods of the present invention in which the tissue desired to be protected is rectal or colonic mucosa—typically, embodiments in which the systemically distributed anticancer therapeutic agent or precursor or metabolite thereof is administered to treat a condition other than colorectal carcinoma—the protectant compositions of the present invention can be formulated for administration by enema.

The compositions of the present invention may be packaged for single use or multiple use, with multiple use packaging usefully designed to provide protectant composition sufficient for the duration of a concurrent course of systemic therapy with anticancer therapeutic agent.

For example, a uracil ointment useful in protecting palmar and plantar surfaces from the toxic effects of systemically distributed fluoropyrimidine or metabolite or prodrug thereof, may usefully be packaged in an amount sufficient for at least a 14-day or 21-day course.

The compositions of the present invention can also usefully be packaged in kits.

The kits of the present invention can, for example, usefully comprise a protectant composition and an orally administrable anticancer therapeutic agent or precursor.

In some embodiments, the invention can comprise a protectant composition formulated for application to a skin surface, such as the palmar and/or plantar skin surface, and an orally administrable fluoropyrimidine, such as tegafur, Carmofur, capecitabine, doxifluridine, UFT, S-1, or Emitefur. In such embodiments, the kit can comprise a plurality of doses of orally administrable fluoropyrimidine, usefully a sufficient number of doses for a standard course of therapy, and a sufficient amount of protectant composition for administration during the course of oral chemotherapy. The plurality of doses of orally administrable fluoropyrimidine can be ganged together, for example in one or more blister packs.

In some of these embodiments, the protectant composition of the kit comprises uracil as the protectant; in certain of these embodiments, uracil is present in a weight/weight percentage of 1.0%.

Embodiments of the kits of the present invention can optionally, but usefully, comprise applicators, particularly in embodiments in which the protectant composition is intended for local administration to a tissue other than the skin surface.

Kits will typically also include instructions for administration of the protectant composition and, if the kit comprises an orally administrable anticancer therapeutic agent or precursor, instructions for oral administration of the oral agent.

In some embodiments, the kits can include dressings, such as occlusive dressings, that facilitate the establishment of a sufficient local concentration of the protectant composition.

The following examples are offered by way of illustration only, and not by way of limitation.

EXAMPLE 1

The theoretical systemic exposure to uracil from the topical application of a 1% w/w uracil ointment to the hands and feet can be crudely estimated as follows.

Application of 0.1 gm of a 1% (w/w) uracil ointment to the hands and feet four times a day represents an exposure of 4-8 mg of uracil/day. The topical absorption of agents through intact skin can be on the order of 1%, leading to a systemic absorption of 40-80 µg/day. This contrasts with exposure of about 1200 mg/day of uracil in UFT. Thus, the mean systemic uracil exposure with uracil ointment averages about 0.00005 (0.005%) that of UFT.

At the skin surface, however, and in the underlying skin, the concentration of uracil should be about 10 mg/ml. The average plasma 5-FU concentration is usefully estimated at 0.5 µg/ml. Thus, topical administration of uracil ointment theoretically establishes a local concentration of uracil that is approximately 2000-fold that of 5-FU at the skin, with a systemic dose only 0.005% that occasioned by oral administration of UFT.

EXAMPLE 2

A 48 year old female patient exhibited metastatic breast cancer. She had refused mastectomy and had previously failed adriamycin and cytoxan, weekly taxol, and weekly navelbine. She was then placed on Xeloda® together with 1% uracil ointment applied to the hands and feet. The 1% uracil ointment was used starting with cycle 5 of treatment with Xeloda®.

Table 1 below summarizes results on this patient.

| Course q3wk | 1 | 2 | 3 | 4 | 5 | 6 | 7 | 8 |
|---|---|---|---|---|---|---|---|---|
| Xeloda dose 14/21 days | 1250 mg/m² bid × 14 | Same | D/C after 4 days | 1000 mg/m² bid × 14 | 1250 mg/m² bid × 14 | Same | Same | Same |
| Taxotere 75 mg/m² | + | + | + | + | + | + | + | + |
| Marker tumor size cm-prior to rx | 12 × 12 | 8 × 8 | 7 × 7 | 7 × 7 | 9 × 9 progression on lower dose Xeloda ® | 8.5 × 8.5 | 8 × 8 | 8.5 × 8.5 |
| 1% uracil ointment | 0 | 0 | 0 | 0 | + | + | + | + |
| Hand-foot syndrome | ND* | ND | ++++ | ++ | 0 | 0 | 0 | 0 |

*ND: Not described

The 1% uracil ointment allowed a re-escalation of the dose of Xeloda® with anti-tumor activity at the higher dose of Xeloda®. The 1% uracil ointment allowed a higher dose of Xeloda® to be administered with improved anti-cancer efficacy (compare columns 5 and 6). The 1% uracil ointment did not have any discernible toxicity.

EXAMPLE 3

Another patient, a 68 year old white female diagnosed with metastatic colon cancer, was treated with Xeloda® and thalidomide. Hand-Foot Syndrome developed. Complete reversal of the syndrome occurred after topical treatment with a 1% uracil ointment. The efficacy of the Xeloda® and thalidomide treatment was unaffected by the concurrent use of 0.1 g 1% uracil ointment four times a day. There were no dose reductions of chemotherapy or treatment delays.

EXAMPLE 4

A 60 year old white female with metastatic colon cancer was treated with 5-FU, Leucovorin®, and Oxaliplatin, a common regime of treatment for this form of cancer. The patient developed hand-foot syndrome.

Topical application of 0.1 g of 1% uracil ointment four time per day resulted in complete resolution of the syndrome. The anti-cancer treatment remained efficacious. No side-effects were noted as a result of the uracil ointment applications. There were no dose reductions of chemotherapy or treatment delays.

In total, 7 patients have been treated with 1% uracil ointment. In no case did hand-foot syndrome develop; there was no observable toxic reaction to the 1% uracil ointment.

EXAMPLE 5

A patient with EGFR expressing metastatic colorectal carcinoma undergoing systemic treatment with cetuximab (ERBITUX®) as single agent therapy develops dermatological toxicity, including skin drying and fissuring and acneform rash.

Cetuximab is a recombinant, human/mouse chimeric monoclonal antibody that binds specifically to the extracellular domain of the human epidermal growth factor receptor (EGFR), competitively inhibiting the binding of epidermal growth factor (EGF) and other ligands, such as transforming growth factor-α.

The patient is treated topically at the site of skin toxicity with 10% EGF (recombinant) in ointment formulation two to four times a day, with reversal of skin toxicity manifestations, permitting the full and unattenuated course of cetuximab to be administered. Systemic absorption of EGF from the topical application of ointment has negligible effect on clinical efficacy of cetuximab therapy.

EXAMPLE 6

A patient being treated with 5-FU by infusion according to the Roswell Park regimen develops diarrhea. The GI toxicity is presumed to result from the local activation of 5-FU by OPRT in the gut.

The patient is treated orally with a daily mixture of 10 mg of orotate together with 10 mg adenine in a slow release capsule formulation; diarrhea is reduced. Orotate, the natural substrate for OPRT, has about a 50-fold lower Km for OPRT than 5-FU at neutral pH. Adenine is included to balance purine (adenine) and pyrimidine (orotate) administration and synthesis. The change in systemic concentration of orotate and adenine is negligible.

EXAMPLE 7

A patient is being treated with bevacizumab (AVASTIN™) in combination with intravenous 5-fluorouracil-based for metastatic carcinoma of the colon. Bevacizumab is a recombinant humanized monoclonal IgG1 antibody that binds to and inhibits the biologic activity of human vascular endothelial growth factor (VEGF).

The patient manifests skin toxicity.

A 1% w/v formulation of VEGF (recombinant) in an ointment formulation is applied to the affected skin areas two to four times per day, with resolution of the skin toxicity and negligible effect on the systemic concentration of VEGF.

EXAMPLE 8

A patient being treated with CPT-11 (CAMPTOSAR®, Irinotecan) for therapy of metastatic colorectal carcinoma manifests serious diarrhea as a toxic side effect of chemotherapy. Irinotecan and its active metabolite SN-38 bind to the topoisomerase I-DNA complex and prevent religation of single-strand breaks.

Aliquots of a mixture of plasmid DNA and topoisomerase I protein are sealed in dialysis membranes having MW cutoff sufficient to retain the protein/DNA complex and admit CPT-11. The patient ingests (without chewing) one such dialysis tubing twice per day, with significant reduction in diarrhea, due to partition of CPT-11 and/or SN38, the active metabolite, into the sealed dialysis membrane, reducing the level of CPT-11 to which the gastrointestinal mucosa is exposed. The reaction between SN38 and topoisomerase I and DNA requires only magnesium.

All patents, patent publications, and other published references mentioned herein are hereby incorporated by reference in their entireties as if each had been individually and specifically incorporated by reference herein.

While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification. The scope of the invention should, therefore, be determined by reference to the appended claims, along with their full scope of equivalents.

I claim:

1. A method of protecting palmar and/or plantar surfaces of a human from the adverse effects associated with the concomitant administration of 5-fluorouracil or a prodrug thereof without abrogating the clinically efficacy of said 5-fluorouracil or a prodrug thereof, comprising:

administering a formulation comprising uracil to the palmar or plantar surfaces in an amount effective to protect against the adverse effects associated with the concomitant administration of 5-fluorouracil or a prodrug thereof.

2. The method of claim 1, wherein the surface is the palmar surface.

3. The method of claim 1, wherein the surface is the plantar surface.

4. The method of claim 1, wherein the amount of uracil effective to protect against the adverse effects of one or more systemically distributed anticancer therapeutic agents or metabolites thereof is at a amount by weight of least about 0.01% and less than about 20%.

5. The method of claim 1, wherein the amount of uracil effective to protect against the adverse effects of one or more systemically distributed anticancer therapeutic agents or metabolites thereof is at a amount by weight of least about 0.01% and less than about 10%.

6. The method of claim 1, wherein the amount of uracil effective to protect against the adverse effects of one or more systemically distributed anticancer therapeutic agents or metabolites thereof is at a amount by weight of least about 0.01% and less than about 5%.

7. The method of claim 1, wherein the amount of uracil effective to protect against the adverse effects of one or more systemically distributed anticancer therapeutic agents or metabolites thereof is at a amount by weight of least about 0.01%.

8. The method of claim 1, wherein the amount of uracil effective to protect against the adverse effects of one or more systemically distributed anticancer therapeutic agents or metabolites thereof is at a amount by weight of least about 0.1%.

9. The method of claim 1, wherein the amount of uracil effective to protect against the adverse effects of one or more systemically distributed anticancer therapeutic agents or metabolites thereof is at a amount by weight of least about 1%.

* * * * *